United States Patent [19]

Fujimoto et al.

[11] Patent Number: 4,554,376

[45] Date of Patent: Nov. 19, 1985

[54] METHOD FOR SEPARATING AND PURIFYING AMINO ACID

[75] Inventors: Teruo Fujimoto; Yoshinobu Isono, both of Nagaoka; Yoshiyuki Miyaki, Shinnanyo, all of Japan

[73] Assignee: Toyo Soda Manufacturing Co., Ltd., Shinnanyo, Japan

[21] Appl. No.: 659,861

[22] Filed: Oct. 11, 1984

Related U.S. Application Data

[63] Continuation of Ser. No. 371,312, Apr. 23, 1982, abandoned.

[30] Foreign Application Priority Data

May 7, 1981 [JP] Japan .................................. 56-67612

[51] Int. Cl.$^4$ .............................................. C07C 99/12
[52] U.S. Cl. .................................................... 562/554
[58] Field of Search ......................................... 562/554

[56] References Cited

U.S. PATENT DOCUMENTS

4,365,023  12/1982  Fujimoto .............................. 521/32

FOREIGN PATENT DOCUMENTS

53-29996  3/1978  Japan .................................. 562/554

OTHER PUBLICATIONS

Eguchi, Maku, 3(5), pp. 367–373, (1978).

Primary Examiner—Michael L. Shippen
Attorney, Agent, or Firm—Armstrong, Nikaido Marmelstein & Kubovcik

[57] ABSTRACT

This is a method for separating or purifying an amino acid from a mixture including other substance such as an inorganic salt other than the amino acid and/or a mutual mixture of amino acids including the amino acid by means of piezo-dialysis employing an amphoteric ion exchange membrane. This membrane is made from a ternary block copolymer having a molecular structure of straight chain in which first macro-molecule with a cation exchange group, second macromolecule with an anion exchange group and third macromolecule without ion exchange group are linked together.

8 Claims, No Drawings

METHOD FOR SEPARATING AND PURIFYING AMINO ACID

This application is a continuation of application Ser. No. 371,312, filed Apr. 23, 1982, now abandoned.

DETAILED DESCRIPTION OF THE INVENTION

This invention relates to a method for separating and purifying an amino acid and more particularly to a method for separating and purifying an amino acid by piezo-dialysis using an amphoteric ion exchange membrane comprising a domain which has a cation exchange group, a domain which has an anion exchange group and another domain which has no ion exchange group.

There have been developed various methods for separating and purifying an amino acid from an amino acid fermented broth containing impurities such as protein, an organic acid, an inorganic salt, a saccharide and a pigment. In most of such conventional methods, an ion-exchange resin is used in combination with a process of crystallization. However, since large quantities of acid, alkali, water, etc. are consumed therein, the conventional methods have presented problems relative to the production cost and waste liquid treatment. Besides, these methods have been rather ineffective for desalting the amino acid. Meanwhile, there has also been developed a method in which electro-dialysis is carried out with a cation exchange membrane and an anion exchange membrane. However, this method necessitates a large electric power consumption.

Heretofore, compound membranes have been studied for use as amphoteric ion exchange membranes. Such studies include a compound membrane which is prepared by embedding beads having cation exchange groups and beads having anion exchange groups alternately in a neutral membrane made of a silicone resin or the like and a compound membrane which is prepared by embedding an anion exchange resin in a cation exchange resin. However, these membranes are not only difficult to prepare but also do not have domains chemically bonding therein. Therefore, their strength is insufficient for piezo-dialysis. The present inventors have discovered that a membrane made from a ternary block copolymer of molecular structure in which a macromolecule having a cation exchange group, a macromolecule having an anion exchange group and a macromolecule having no ion exchange group are bonded together in a straight chain like state is capable of allowing a low molecular weight electrolyte to permeate it through piezo-dialysis; and that, by utilizing this property of the membrane, an amino acid can be separated and purified. The above stated ternary block copolymer, in the form of a film, forms a micro-phase separated structure which consists of three phases of a size close to the molecular size thereof. As a result of this, a domain having a cation exchange group and a domain having an anion exchange group exist separately from each other. Accordingly, the film functions as amphoteric ion exchange membrane.

It is known that generally a blend of a macromolecule having a cation exchange group and a macromolecule having an anion exchange group forms a neutral complex called a poly-ion complex. Partial or perfect salt formation similar to this takes place also in the case of a binary block copolymer consisting of a cation exchange group and an anion exchange group. Then, the film of the binary block copolymer does not function well as ion exchanger. Whereas, the film according to the present invention is made from a ternary block copolymer containing a neutral segment. With the film material thus arranged, a domain having a cation exchange group and a domain having an anion exchange group are separated from each other and are thus prevented from forming a poly-ion complex.

The method of the invention hereinafter will be described in further detail. In accordance with the method of the present invention, amino acids are separated from each other and/or an amino acid is purified by carrying out piezo-dialysis with a compound membrane made from a ternary block copolymer consisting of segments in which a constituent has a cation exchange group and another constituent has an anion exchange group while a remaining constituent has no ion exchange group. In carrying out the invented method, an amino acid containing solution to be used as crude material has an amino acid concentration between 0.1 g/dl and 30 g/dl. Pressure to be applied is between 10 kg/cm$^2$ and 150 kg/cm$^2$ and is preferably 30 kg/cm$^2$ and more. The pressure must be sufficient for overcoming osmotic pressure acting between the two faces of the film and is within a range permissible by the dialyzing apparatus and the strength of the film. Therefore, the pressure required varies with the concentration of the impurities such as inorganic salts, etc. contained in the crude material solution.

To carry out the piezo-dialysis, the pH of the crude material solution is determined at a suitable value within a range from 2 to 13 according to the kind of the amino acid to be separated and purified. At the isoelectric point of the amino acid, the electric charge of the amino acid apparently becomes zero. Therefore, when the dialysis is carried out at the isoelectric point, a low molecular weight electrolyte which is contained as an impurity in an amino acid solution or an amino acid which is not at an isoelectric point can be selectively allowed to permeate while an amino acid which is at an isoelectric point can be prevented from permeating. Accordingly, the invented method is not only effective for removing impurities contained in the amino acid such as protein, an organic acid, a saccharide, an inorganic salt and organic matters but also effective for separating amino acids of different isoelectric points from each other.

To desalt an amino acid, piezo-dialysis is carried out at a pH adjusted to the isoelectric point of the amino acid. Further, to separate a desired amino acid from an amino acid fermented broth, piezo-dialysis is first carried out at the isoelectric point of the amino acid to remove a low molecular weight electrolyte and then piezo-dialysis is again carried out by adjusting the pH to a region other than the isoelectric point and vice versa.

Among the segments constituting the ternary block copolymer to be used in accordance with the invented method, the constituent segment which forms a domain having a cation exchange group may be selected from polymers of unsaturated carboxylic acid esters or cyano group containing monomers such as acrylonitrile, styrene or α-methyl styrene. The constituent segment which forms a domain having an anion exchange group may be selected from polymers of compounds having heterocyclic rings containing nitrogen atoms such as vinyl pyridine, vinyl pyrimidine, or vinyl quinoline and polymers of styrene derived amines such as a vnyl benzyl dialkyl amine. These polymers permit introduction of a cation exchange group or an anion exchange group without difficulty by known methods such as methods of carrying out hydrolysis, sulfonation, quaternization, etc. The remaining constituent segment which forms a domain having no ion exchange group is preferably selected from diene polymers such as butadiene, isoprene, etc. The strength of the film can be increased by crosslinking this segment. Further, the amount of this neutral domain contained in the ternary block copolymer is preferably between 30 and 90%. With regard to the ternary block copolymer, the present applicant previously filed a U.S. patent application Ser. No. 206,562 filed Nov. 13, 1980, now U.S. Pat. No. 4,365,023, under the tile of "Block Copolymer."

Assuming that the segment which is capable of introducing a cation exchange group is expressed as "poly A," the segment which is capable of introducing an anion exchange group as "poly B" and the segment which is not introducing any ion exchange group as "poly C," since dialysis is to be carried out under pressure, the blocks of the block copolymer to be used for a membrane for separating and purifying an amino acid are preferably arranged to have the cation segment and the anion segment separated from each other by the neutral segment in such a manner as poly A-poly C-poly B; poly C-poly A-poly C-poly B; poly A-poly C-poly B-poly C; or poly C-poly A-poly C-poly B-poly C. Arrangement to have the cation segment and the anion segment adjacent to each other in such a manner as poly A-poly B-poly C tends to impair the separating efficiency of the membrane. Meanwhile, even if each of the cation, anion and neutral segments is a copolymer consisting of two or more kinds of monomers, it would make no difference in the results obtainable in accordance with the invention.

The invention will more fully be understood from the following description of embodiment examples. However, it is to be understood that the present invention is not limited to these examples. Futher, it is apparent from the results obtained in accordance with the invention that the amphoteric ion exchange membrane which is composed of the ternary block copolymer is not only applicable to amino acids but also readily usable for separation of a low molecular weight electrolyte and a low molecular weight non-electrolyte from each other in general.

EXAMPLE 1

Using n-butyl lithium as initiator, polymerization was carried out in benzene in the sequence of isoprene, styrene, isoprene, p-vinyl-benzyl dimethyl amine and isoprene to obtain a ternary block copolymer of molecular weight about $2 \times 10^5$ g/ml. The ratio by weight of the monomers were arranged to be 7.3:14.4:7.1:25:6.9. The copolymer thus obtained was cast from a benzene solution into a film of thickness about 50 $\mu$m. After that the isoprene portion of the copolymer was crosslinked by sulfur monochloride. The amine portion was quartenized in the vapor of methyl iodide. Further, the styrene portion was sulfonated with chloro-sulfonic acid. Through these processes, cation and anion exchange groups were introduced to obtain an amphoteric ion exchange membrane. Then, using the membrane, piezo-dialytic experiments were carried out for an aqueous solution which was prepared by dissolving 0.1 g/dl of glycine in a buffer solution containing 2% of sodium chloride. The pressure was set at 30 atm. The pH was varied between 2 and 12. The water flux was 0.38 ml/min-cm$^2$. The concentration of sodium chloride in the permeate was determined by measuring chloride ion and that of glycine was by an amino acid analyser. It was found that the rejection for the sodium chloride was about 0% irrespectively of pH and that the rejection for glycine showed its maximum value of 90% in the vicinity of pH=6 which was the isoelectric point of glycine while the rejection saliently decreased in the regions of pH values above and below 6. Therefore, it was found that desalination from a glycine containing solution was possible with piezo-dialysis carried out at a pH value of 6.

EXAMPLE 2

Piezo-dialytic experiments were carried out in the same manner as in Example 1 with the exception of that the glycine was replaced with glutamic acid. The results of experiments showed that: The rejection for sodium chloride was about 0% irrespectively of the pH value. The rejection for the glutamic acid was about 90% in the vicinity of pH=3 which is close to the isoelectric point thereof while the rate saliently decreased in the pH region higher than this pH value.

EXAMPLE 3

Piezo-dialytic experiments were carried out at pressure of 30 atm and a pH value of 6 using the same film as the film used in Example 1 for an aqueous solution containing 0.1 g/dl of glycine and 0.1 g/dl of glutamic acid. The rejection for glycine was almost 100% while the rejection for glutamic acid was close to 0%. When the piezo-dialytic experiment was carried out at a pH value of 3, the rejection for the two reversed. This facts indicates that the glycine and the glutamic acid can be separated by carrying out piezo-dialysis at a pH value of 6 or 3.

COMPARISON EXAMPLE 1

A film of thickness about 100 $\mu$m was obtained by casting a benzene solution of a binary block copolymer consisting of equimolecular styrene and p-vinyl benzyl dimethyl amine. The amine portion of the film was quaternized and the styrene portion thereof was sulfonated by the same method as in Example 1. Then, by using a membrane thus obtained, piezo-dialytic experiments were carried out in the same manner as in Example 1. However, the sodium chloride and the glycine hardly permeated in any region of pH. This was believed to be caused by formation of a poly-ion complex, which prevented the film from functioning as amphoteric ion exchanger.

We claim:

1. A method for purifying an amino acid comprising performing piezo-dialysis of a mixture containing said amino acid and a substance other than said amino acid to produce the purified amino acid, said piezo-dialysis being carried out using an amphoteric ion exchange membrane composed of a ternary block copolymer having a molecular structure in which a macromolecule having a cation exchange group, a macromolecule having an anion exchange group and a macromolecule having no ion exchange group are linked together to form a straight chain and in which the macromolecule having the cation exchange group are separated from each other by the macromolecule having no ion exchange group with the segments of the macromolecules having one of the following sequences, poly A-poly C-poly B; poly C-poly A-poly C-poly B-poly C; poly A-poly C-poly B-poly C and poly C-poly A-poly C-poly B wherein the segment having the cation exchange group is poly A, the segment having the anion exchange group poly B and the neutral segment is poly C.

2. The method for purifying an amino acid according to claim 1 wherein said substance other than said amino acid is another amino acid, a protein, an organic acid, a saccharide, an inorganic salt, or a mixture thereof.

3. The method for purifying an amino acid according to claim 1 wherein the macromolecule having no ion exchange group comprises 30 to 90% by weight of the ternary block copolymer.

4. A method for purifying amino acid as in claim 1, further comprising a process for removing a desired amino acid from a mother liquor thereof by conducting a piezo-dialysis of the mother liquor while maintaining the pH thereof in a region other than the isoelectric point of said amino acid.

5. A method for purifying amino acid as in claim 1, further comprising a process for removing species of inorganic or organic ions contained in a mother liquor thereof by conducting a piezo-dialysis of said mother liquor containing a desired amino acid while maintaining the pH thereof in the isoelectric point of said amino acid.

6. The method of purifying an amino acid as defined in claim 1 wherein the macromolecule having the cation exchange group is selected from at least one of the following; polymers of unsaturated carboxylic acid esters, and cyano group containing monomers.

7. The method of purifying an amino acid as defined in claim 1 wherein the macromolecule having the anion exchange group is selected from at least one of the following; polymers of compounds having heterocyclic rings containing nitrogen atoms and polymers of styrene derived amines.

8. The method of purifying an amino acid as defined in claim 1 wherein the macro molecule having no ion exchange group is a diene polymer.

* * * * *